US008968340B2

(12) United States Patent
Chowaniec et al.

(10) Patent No.: US 8,968,340 B2
(45) Date of Patent: Mar. 3, 2015

(54) SINGLE ACTUATING JAW FLEXIBLE ENDOLUMENAL STITCHING DEVICE

(75) Inventors: Matthew Chowaniec, Middletown, CT (US); Eric Taylor, East Hampton, CT (US); Peter Hathaway, Lebanon, CT (US)

(73) Assignee: Covidien LP, Mansfield, MA (US)

( * ) Notice: Subject to any disclaimer, the term of this patent is extended or adjusted under 35 U.S.C. 154(b) by 402 days.

(21) Appl. No.: 13/364,353

(22) Filed: Feb. 2, 2012

(65) Prior Publication Data

US 2012/0215234 A1      Aug. 23, 2012

Related U.S. Application Data

(60) Provisional application No. 61/445,568, filed on Feb. 23, 2011.

(51) Int. Cl.
*A61B 17/04* (2006.01)
*A61B 17/062* (2006.01)
*A61B 17/00* (2006.01)
*A61B 17/06* (2006.01)
*A61B 17/29* (2006.01)

(52) U.S. Cl.
CPC ......... *A61B 17/0625* (2013.01); *A61B 17/0469* (2013.01); *A61B 2017/00314* (2013.01); *A61B 2017/06047* (2013.01); *A61B 2017/2934* (2013.01); *A61B 2017/2941* (2013.01)
USPC ....................................................... 606/144

(58) Field of Classification Search
CPC .............................................. A61B 2017/2926
See application file for complete search history.

(56) References Cited

U.S. PATENT DOCUMENTS

| | | |
|---|---|---|
| 1,822,330 A | 9/1931 | Ainslie |
| 2,327,353 A | 8/1943 | Karle |
| 3,073,311 A | 1/1963 | Tibbs et al. |
| 3,123,077 A | 3/1964 | Alcamo |
| 4,236,470 A | 12/1980 | Stenson |
| 4,890,615 A | 1/1990 | Caspari et al. |
| 4,923,461 A | 5/1990 | Caspari et al. |
| 4,935,027 A | 6/1990 | Yoon |

(Continued)

FOREIGN PATENT DOCUMENTS

| | | |
|---|---|---|
| DE | 44 23 881 C1 | 10/1995 |
| EP | 0 592 244 A2 | 4/1994 |

(Continued)

OTHER PUBLICATIONS

International Search Report for PCT/US07/021506 date of completion Mar. 10, 2008 (2 pages).

(Continued)

*Primary Examiner* — Tuan V Nguyen (57) ABSTRACT

An end effector for use in an endoscopic stitching device includes a fixed jaw, a moveable jaw, a linkage member, needle engaging blades and a rotatable member. The moveable jaw is pivotably associated with the fixed jaw about a first pivot axis. The linkage member is pivotably associated with the moveable jaw about a second pivot axis. The needle engaging blade is slidably supported in each of the fixed and moveable jaws. An axial movement of the linkage member causes the moveable jaw to pivot about the first pivot axis with respect to the fixed jaw, and rotation of the rotatable member causes opposed axial movement of the pair of needle engaging blades.

14 Claims, 8 Drawing Sheets

(56) References Cited

U.S. PATENT DOCUMENTS

| | | | |
|---|---|---|---|
| 5,037,433 | A | 8/1991 | Wilk et al. |
| 5,042,707 | A | 8/1991 | Taheri |
| 5,080,663 | A | 1/1992 | Mills et al. |
| 5,100,421 | A | 3/1992 | Christoudias |
| 5,100,430 | A | 3/1992 | Aveillanet et al. |
| 5,209,747 | A | 5/1993 | Knoepfler |
| 5,271,543 | A | 12/1993 | Grant et al. |
| 5,300,082 | A | 4/1994 | Sharpe et al. |
| 5,308,353 | A | 5/1994 | Beurrier |
| 5,314,446 | A | 5/1994 | Hunter et al. |
| 5,330,502 | A | 7/1994 | Hassler et al. |
| 5,336,229 | A | 8/1994 | Noda |
| 5,350,391 | A | 9/1994 | Iacovelli |
| 5,358,498 | A | 10/1994 | Shave |
| 5,374,277 | A | 12/1994 | Hassler |
| 5,387,221 | A | 2/1995 | Bisgaard |
| 5,389,103 | A | 2/1995 | Melzer et al. |
| 5,391,176 | A | 2/1995 | de la Torre |
| 5,403,342 | A | 4/1995 | Tovey et al. |
| 5,405,352 | A | 4/1995 | Weston |
| 5,439,478 | A | 8/1995 | Palmer |
| 5,454,823 | A | 10/1995 | Richardson et al. |
| 5,454,827 | A | 10/1995 | Aust et al. |
| 5,472,446 | A | 12/1995 | de la Torre |
| 5,478,344 | A | 12/1995 | Stone et al. |
| 5,480,406 | A | 1/1996 | Nolan et al. |
| 5,496,334 | A | 3/1996 | Klundt et al. |
| 5,527,323 | A | 6/1996 | Jervis et al. |
| 5,540,703 | A | 7/1996 | Barker, Jr. et al. |
| 5,540,706 | A | 7/1996 | Aust et al. |
| 5,549,617 | A | 8/1996 | Green et al. |
| 5,549,637 | A | 8/1996 | Crainich |
| 5,562,686 | A | 10/1996 | Sauer et al. |
| 5,564,615 | A | 10/1996 | Bishop et al. |
| 5,571,090 | A | 11/1996 | Sherts |
| 5,573,286 | A | 11/1996 | Rogozinski |
| 5,575,799 | A | 11/1996 | Bolanos et al. |
| 5,582,617 | A | 12/1996 | Klieman et al. |
| 5,591,181 | A | 1/1997 | Stone et al. |
| 5,601,224 | A | 2/1997 | Bishop et al. |
| 5,620,415 | A | 4/1997 | Lucey et al. |
| 5,628,756 | A | 5/1997 | Barker, Jr. et al. |
| 5,630,825 | A | 5/1997 | de la Torre et al. |
| 5,632,751 | A | 5/1997 | Piraka |
| 5,643,293 | A | 7/1997 | Kogasaka et al. |
| 5,643,294 | A | 7/1997 | Tovey et al. |
| 5,662,666 | A | 9/1997 | Onuki et al. |
| 5,674,229 | A | 10/1997 | Tovey et al. |
| 5,674,230 | A | 10/1997 | Tovey et al. |
| 5,681,331 | A | 10/1997 | de la Torre et al. |
| 5,690,652 | A | 11/1997 | Wurster et al. |
| 5,690,653 | A | 11/1997 | Richardson et al. |
| 5,702,408 | A | 12/1997 | Wales et al. |
| 5,715,942 | A | 2/1998 | Li et al. |
| 5,728,107 | A | 3/1998 | Zlock et al. |
| 5,728,109 | A | 3/1998 | Schulze et al. |
| 5,728,113 | A | 3/1998 | Sherts |
| 5,730,747 | A | 3/1998 | Ek et al. |
| 5,746,751 | A | 5/1998 | Sherts |
| 5,749,898 | A | 5/1998 | Schulze et al. |
| 5,752,973 | A | 5/1998 | Kieturakis |
| 5,755,729 | A | 5/1998 | de la Torre et al. |
| 5,759,188 | A | 6/1998 | Yoon |
| 5,766,196 | A | 6/1998 | Griffiths |
| 5,779,646 | A | 7/1998 | Koblish et al. |
| 5,792,153 | A | 8/1998 | Swain et al. |
| 5,792,165 | A | 8/1998 | Klieman et al. |
| 5,797,537 | A | 8/1998 | Oberlin et al. |
| 5,797,927 | A | 8/1998 | Yoon |
| 5,797,928 | A | 8/1998 | Kogasaka |
| 5,814,054 | A | 9/1998 | Kortenbach et al. |
| 5,814,069 | A | 9/1998 | Schulze et al. |
| 5,817,119 | A | 10/1998 | Klieman et al. |
| 5,827,323 | A | 10/1998 | Klieman et al. |
| 5,865,836 | A | 2/1999 | Miller |
| 5,871,488 | A | 2/1999 | Tovey et al. |
| 5,876,412 | A | 3/1999 | Piraka |
| 5,893,592 | A | 4/1999 | Schulze et al. |
| 5,897,563 | A | 4/1999 | Yoon et al. |
| 5,906,630 | A | 5/1999 | Anderhub et al. |
| 5,908,428 | A | 6/1999 | Scirica et al. |
| 5,911,727 | A | 6/1999 | Taylor |
| 5,928,136 | A | 7/1999 | Barry |
| 5,931,855 | A | 8/1999 | Buncke |
| 5,938,668 | A | 8/1999 | Scirica et al. |
| 5,941,430 | A | 8/1999 | Kuwabara |
| 5,947,982 | A | 9/1999 | Duran |
| 5,954,731 | A | 9/1999 | Yoon |
| 5,954,733 | A | 9/1999 | Yoon |
| 5,957,937 | A | 9/1999 | Yoon |
| 5,980,538 | A | 11/1999 | Fuchs et al. |
| 5,984,932 | A | 11/1999 | Yoon |
| 5,993,457 | A | 11/1999 | Yoon |
| 5,993,466 | A | 11/1999 | Yoon |
| 5,993,467 | A | 11/1999 | Yoon |
| 5,997,565 | A | 12/1999 | Inoue |
| 6,004,332 | A | 12/1999 | Yoon et al. |
| 6,017,358 | A | 1/2000 | Yoon et al. |
| 6,027,522 | A | 2/2000 | Palmer |
| 6,051,006 | A | 4/2000 | Shluzas et al. |
| 6,071,289 | A | 6/2000 | Stefanchik et al. |
| 6,077,287 | A | 6/2000 | Taylor et al. |
| 6,080,180 | A | 6/2000 | Yoon |
| 6,086,601 | A | 7/2000 | Yoon |
| 6,119,913 | A | 9/2000 | Adams et al. |
| 6,126,665 | A | 10/2000 | Yoon |
| 6,126,666 | A | 10/2000 | Trapp et al. |
| 6,139,563 | A | 10/2000 | Cosgrove, III et al. |
| 6,143,005 | A | 11/2000 | Yoon et al. |
| 6,171,316 | B1 | 1/2001 | Kovac et al. |
| 6,206,893 | B1 | 3/2001 | Klein et al. |
| 6,214,028 | B1 | 4/2001 | Yoon et al. |
| 6,223,100 | B1 | 4/2001 | Green |
| 6,224,614 | B1 | 5/2001 | Yoon |
| 6,261,207 | B1 | 7/2001 | Yoon et al. |
| 6,261,307 | B1 | 7/2001 | Yoon et al. |
| 6,277,132 | B1 | 8/2001 | Brhel |
| 6,319,262 | B1 | 11/2001 | Bates et al. |
| 6,332,889 | B1 | 12/2001 | Sancoff et al. |
| 6,346,111 | B1 | 2/2002 | Gordon et al. |
| 6,358,259 | B1 | 3/2002 | Swain et al. |
| 6,494,888 | B1 | 12/2002 | Laufer et al. |
| 6,506,196 | B1 | 1/2003 | Laufer |
| 6,517,539 | B1 | 2/2003 | Smith et al. |
| 6,533,796 | B1 | 3/2003 | Sauer et al. |
| 6,569,105 | B1 | 5/2003 | Kortenbach et al. |
| 6,582,450 | B2 | 6/2003 | Ouchi |
| 6,596,015 | B1 | 7/2003 | Pitt et al. |
| 6,599,310 | B2 | 7/2003 | Leung et al. |
| 6,638,287 | B2 | 10/2003 | Danitz et al. |
| 6,663,639 | B1 | 12/2003 | Laufer et al. |
| 6,663,641 | B1 | 12/2003 | Kovac et al. |
| 6,666,854 | B1 | 12/2003 | Lange |
| 6,676,676 | B2 | 1/2004 | Danitz et al. |
| 6,719,764 | B1 | 4/2004 | Gellman et al. |
| 6,719,765 | B2 | 4/2004 | Bonutti |
| 6,743,239 | B1 | 6/2004 | Kuehn et al. |
| 6,743,240 | B2 | 6/2004 | Smith et al. |
| 6,755,843 | B2 | 6/2004 | Chung et al. |
| 6,773,441 | B1 | 8/2004 | Laufer et al. |
| 6,786,913 | B1 | 9/2004 | Sancoff et al. |
| 6,821,285 | B2 | 11/2004 | Laufer et al. |
| 6,835,200 | B2 | 12/2004 | Laufer et al. |
| 6,889,116 | B2 | 5/2005 | Jinno |
| 6,936,054 | B2 | 8/2005 | Chu |
| 6,936,061 | B2 | 8/2005 | Sasaki |
| 6,955,643 | B2 | 10/2005 | Gellman et al. |
| 6,972,017 | B2 | 12/2005 | Smith et al. |
| 6,981,628 | B2 | 1/2006 | Wales |
| 6,991,635 | B2 | 1/2006 | Takamoto et al. |
| 6,997,931 | B2 | 2/2006 | Sauer et al. |
| 7,011,668 | B2 | 3/2006 | Sancoff et al. |
| 7,037,315 | B2 | 5/2006 | Sancoff et al. |
| 7,041,111 | B2 | 5/2006 | Chu |

(56) References Cited

U.S. PATENT DOCUMENTS

| | | |
|---|---|---|
| 7,052,489 B2 | 5/2006 | Griego et al. |
| RE39,152 E | 6/2006 | Aust et al. |
| 7,063,710 B2 | 6/2006 | Takamoto et al. |
| 7,063,715 B2 | 6/2006 | Onuki et al. |
| 7,107,124 B2 | 9/2006 | Green |
| 7,153,314 B2 | 12/2006 | Laufer et al. |
| 7,191,900 B2 | 3/2007 | Opie et al. |
| 7,192,437 B2 | 3/2007 | Shalaby |
| 7,211,093 B2 | 5/2007 | Sauer et al. |
| 7,218,972 B2 | 5/2007 | Rodriguez |
| 7,232,448 B2 | 6/2007 | Battles et al. |
| 7,244,260 B2 | 7/2007 | Koseki |
| 7,248,944 B2 | 7/2007 | Green |
| 7,468,068 B2 | 12/2008 | Kolster |
| 7,601,164 B2 | 10/2009 | Wu |
| 7,645,284 B2 | 1/2010 | Burbank et al. |
| 7,666,194 B2 | 2/2010 | Field et al. |
| 7,691,112 B2 | 4/2010 | Chanduszko et al. |
| 7,704,261 B2 | 4/2010 | Sakamoto et al. |
| 7,708,747 B2 | 5/2010 | Bjerken |
| 7,722,630 B1 | 5/2010 | Stone et al. |
| 7,731,726 B2 | 6/2010 | Belhe et al. |
| 7,736,372 B2 | 6/2010 | Reydel et al. |
| 7,758,597 B1 | 7/2010 | Tran et al. |
| 7,758,598 B2 | 7/2010 | Conlon et al. |
| 7,766,925 B2 | 8/2010 | Stokes et al. |
| 7,771,438 B2 | 8/2010 | Dreyfuss et al. |
| 7,776,059 B2 | 8/2010 | Craig |
| 7,776,066 B2 | 8/2010 | Onuki et al. |
| 7,780,701 B1 | 8/2010 | Meridew et al. |
| 7,784,612 B2 | 8/2010 | Kanda et al. |
| 7,798,325 B2 | 9/2010 | Wizemann et al. |
| 7,814,630 B2 | 10/2010 | Price et al. |
| 7,815,654 B2 | 10/2010 | Chu |
| 7,815,659 B2 | 10/2010 | Conlon et al. |
| 7,828,812 B2 | 11/2010 | Stokes et al. |
| 7,833,235 B2 | 11/2010 | Chu |
| 7,833,237 B2 | 11/2010 | Sauer |
| 7,837,696 B2 | 11/2010 | Modesitt et al. |
| 7,842,047 B2 | 11/2010 | Modesitt et al. |
| 7,842,048 B2 | 11/2010 | Ma |
| 7,846,170 B2 | 12/2010 | Modesitt et al. |
| 7,850,701 B2 | 12/2010 | Modesitt et al. |
| 7,883,517 B2 | 2/2011 | Pantages et al. |
| 7,883,519 B2 | 2/2011 | Oren et al. |
| 7,887,554 B2 | 2/2011 | Stokes et al. |
| 7,935,128 B2 | 5/2011 | Rioux et al. |
| 7,947,052 B2 | 5/2011 | Baxter, III et al. |
| 7,947,053 B2 | 5/2011 | McKay et al. |
| 7,951,157 B2 | 5/2011 | Gambale |
| 7,967,832 B2 | 6/2011 | Chu |
| 7,967,842 B2 | 6/2011 | Bakos |
| 7,972,344 B2 | 7/2011 | Murray et al. |
| 7,976,552 B2 | 7/2011 | Suzuki |
| 2002/0010480 A1 | 1/2002 | Sancoff et al. |
| 2002/0065526 A1 | 5/2002 | Oren et al. |
| 2002/0072702 A1 | 6/2002 | Quay |
| 2002/0128666 A1 | 9/2002 | Sancoff et al. |
| 2002/0173800 A1 | 11/2002 | Dreyfuss et al. |
| 2002/0198542 A1 | 12/2002 | Yamamoto et al. |
| 2003/0009195 A1 | 1/2003 | Field et al. |
| 2003/0014077 A1 | 1/2003 | Leung et al. |
| 2003/0045891 A1 | 3/2003 | Yamamoto et al. |
| 2003/0105475 A1 | 6/2003 | Sancoff et al. |
| 2003/0105476 A1 | 6/2003 | Sancoff et al. |
| 2003/0114863 A1 | 6/2003 | Field et al. |
| 2003/0116670 A1 | 6/2003 | Gentry |
| 2003/0171761 A1 | 9/2003 | Sancoff et al. |
| 2003/0233104 A1 | 12/2003 | Gellman et al. |
| 2004/0010245 A1 | 1/2004 | Cerier et al. |
| 2004/0060410 A1 | 4/2004 | Leung et al. |
| 2004/0068272 A1 | 4/2004 | Sauer et al. |
| 2004/0087976 A1 | 5/2004 | DeVries et al. |
| 2004/0092967 A1 | 5/2004 | Sancoff et al. |
| 2004/0181243 A1 | 9/2004 | Chu et al. |
| 2004/0193186 A1 | 9/2004 | Kortenbach et al. |
| 2004/0199184 A1 | 10/2004 | Topper et al. |
| 2005/0043747 A1 | 2/2005 | Field et al. |
| 2005/0085832 A1 | 4/2005 | Sancoff et al. |
| 2005/0096694 A1 | 5/2005 | Lee |
| 2005/0126876 A1 | 6/2005 | Simmons |
| 2005/0165419 A1 | 7/2005 | Sauer et al. |
| 2005/0256533 A1 | 11/2005 | Roth et al. |
| 2006/0025817 A1 | 2/2006 | Ortiz et al. |
| 2006/0036232 A1 | 2/2006 | Primavera et al. |
| 2006/0069396 A1 | 3/2006 | Meade et al. |
| 2006/0111209 A1 | 5/2006 | Hinman et al. |
| 2006/0235304 A1 | 10/2006 | Harhen et al. |
| 2006/0253126 A1 | 11/2006 | Bjerken et al. |
| 2006/0282093 A1 | 12/2006 | Shelton et al. |
| 2006/0283093 A1 | 12/2006 | Shelton, IV et al. |
| 2007/0005110 A1 | 1/2007 | Collier et al. |
| 2008/0188868 A1 | 8/2008 | Weitzner et al. |
| 2008/0312688 A1 | 12/2008 | Nawrocki et al. |

FOREIGN PATENT DOCUMENTS

| | | |
|---|---|---|
| EP | 0 647 431 A | 4/1995 |
| EP | 1 481 628 A1 | 12/2004 |
| EP | 1 915 957 A2 | 4/2008 |
| EP | 1 915 966 A1 | 4/2008 |
| EP | 2 044 890 A1 | 4/2009 |
| WO | WO 98/11814 A2 | 3/1998 |
| WO | WO 98/11829 A1 | 3/1998 |
| WO | WO 98/53745 A1 | 12/1998 |
| WO | WO 99/15090 A1 | 4/1999 |
| WO | WO 99/18859 A1 | 4/1999 |
| WO | WO 00/67834 A1 | 11/2000 |
| WO | WO 01/74254 A | 10/2001 |
| WO | WO 02/34147 A1 | 5/2002 |
| WO | WO 03/017850 A | 3/2003 |
| WO | WO 2006/061868 A | 6/2006 |
| WO | WO 2008/042423 A2 | 4/2008 |
| WO | WO 2008/045333 A | 4/2008 |

OTHER PUBLICATIONS

European Search Report for EP 123169361.8 date of completion Jul. 24, 2012 (9 pages).

European Search Report for EP 07839357.6 date of completion Oct. 31, 2012 (10 pages).

European Search Report for EP 09251544.4 mailed Feb. 28, 2013 (18 pgs.).

SINGLE ACTUATING JAW FLEXIBLE ENDOLUMENAL STITCHING DEVICE

CROSS-REFERENCE TO RELATED APPLICATIONS

The present application claims the benefit of and priority to U.S. Provisional Application Ser. No. 61/445,568, filed Feb. 23, 2011, the entire content of which is incorporated herein by reference.

BACKGROUND

1. Technical Field

The present disclosure relates to a device for endoscopic suturing or stitching, and, more particularly, to an end effector for endoscopic suturing or stitching through an access tube.

2. Background of Related Art

Generally, endoscopic surgery involves incising through body walls for viewing and/or operating on a particular organ, such as, for example, the ovaries, uterus, gall bladder, bowels, kidneys, and appendix. Typically, trocars are utilized for creating an incision through which the endoscopic surgery is performed. Trocar tubes or cannula devices are extended into and left in place in the abdominal wall to provide access for endoscopic surgical tools. A camera or endoscope is inserted through a relatively large diameter trocar tube, which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas.

In many surgical procedures, including those involved in endoscopic surgery, it is often necessary to suture bodily organs or tissue. In the past, suturing of bodily organs or tissue through endoscopic surgery was achieved through the use of a sharp metal suture needle which had attached at one of its ends a length of suture material. The surgeon would cause the suture needle to penetrate and pass through bodily tissue, pulling the suture material through the bodily tissue. Once the suture material was pulled through the bodily tissue, the surgeon proceeded to tie a knot in the suture material. The knotting of the suture material allowed the surgeon to adjust the tension on the suture material to accommodate the particular tissue being sutured and control approximation, occlusion, attachment or other conditions of the tissue. The ability to control tension is extremely important to the surgeon regardless of the type of surgical procedure being performed. However, during endoscopic surgery, knotting of the suture material is time consuming and burdensome due to the difficult maneuvers and manipulation which are required through the small endoscopic openings.

Accordingly, a need exists for improved surgical stitching devices for conducting endoluminal stitching and the like.

SUMMARY

In accordance with the present disclosure, an end effector of an endoscopic stitching device includes a fixed jaw, a moveable jaw, a coupler, a linkage member, needle engaging blades and a rotatable member. The moveable jaw is pivotably associated with the fixed jaw and is pivotable about a first pivot axis. Each jaw defines a needle receiving recess formed in a tissue contacting surface thereof and a longitudinal channel in communication with the needle receiving recess. The linkage member is pivotably associated with the moveable jaw about a second pivot axis. Each needle engaging blade is slidably supported in each of the fixed jaw and the moveable jaw. Each blade is axially translatable in the longitudinal channel between a first position in which the blade partially extends across the needle receiving recess and a second position in which the blade does not extend across the needle receiving recess. The rotatable member defines a helical groove in an outer surface thereof. A proximal end of each blade is configured for slidable engagement in the helical groove, wherein the blades are disposed on opposed sides of the rotatable member. An axial movement of the coupler causes the curvilinear movement of the linkage member resulting in the moveable jaw to pivot about the first pivot axis with respect to the fixed jaw, and rotation of the rotatable member causes opposite axial movement of the pair of needle engaging blades with respect to each other.

In an embodiment, the end effector may further include a lead screw operatively coupled to the coupler, wherein rotation of the lead screw causes axial movement of the coupler.

In addition, the coupler may be pivotally connected to the linkage member such that rotation of lead screw, relative to the coupler, axially displaces coupler and pivots the moveable jaw about the first pivot axis.

The end effector may further include a jaw support member defining a longitudinal axis, wherein the fixed jaw is securely fixed to the jaw support member. The jaw support member may define a lumen configured to rotatably support the rotatable member therein and a pair of grooves configured to slidably receive respective needle engaging blades.

The first pivot axis may be disposed on the longitudinal axis defined by the jaw support member. The second pivot axis may be offset from the longitudinal axis defined by the jaw support member. It is also contemplated that the moveable jaw may define a second longitudinal axis and that the first pivot axis be spaced a first transverse distance from a second longitudinal axis. The second pivot axis may be spaced a second transverse distance from the second longitudinal axis. The second transverse distance may be greater than the first transverse distance. The first pivot axis and the second pivot axis may be parallel to one another.

In another embodiment, the lead screw may include an annular flange projecting radially outward for rotatable engagement with the jaw support member. The jaw support member may define an inner circumferential groove for receiving the annular flange of the lead screw therein. The end effector may further include an actuation cable coupled to the linkage member. The actuation cable may be slidably movable through a longitudinal bore defined in the rotatable member. Uni-directional rotation of the rotatable member results in axial translation of the pair of needle engaging blades in opposite directions with respect to each other.

In accordance with still another embodiment of the present disclosure, an end effector for use in an endoscopic stitching device includes a fixed jaw, a moveable jaw, a coupler, a linkage member, needle engaging blades, a hub, a pair of opposing cuffs, and a pair of wires. The moveable jaw is pivotably associated with the fixed jaw and is pivotable about a first pivot axis. Each jaw defines a needle receiving recess formed in a tissue contacting surface thereof and a longitudinal channel in communication with the needle receiving recess. The linkage member is pivotably associated with the moveable jaw about a second pivot axis. Each needle engaging blade is slidably supported in each of the fixed jaw and the moveable jaw. Each blade is axially translatable in the longitudinal channel between a first position in which the blade partially extends across the needle receiving recess and a second position in which the blade does not extend across the needle receiving blade. The hub defines a central lumen therethrough. Each cuff partially surrounds the hub and is configured for axial translation. The pair of wires operatively actuates the needle engaging blades. Each cuff is coupled to one of the pair of needle engaging blades and a respective one of the pair of wires. An axial movement of the pair of wires causes axial movement of the pair of needle engaging blades and an axial movement of the linkage member causes the moveable jaw to pivot about the first pivot axis with respect to the fixed jaw.

In still another embodiment, the pair of opposing cuffs may be configured for independent axial translation with respect to each other. The pair of needle engaging blades may be coaxially arranged with respect to respective wire of the pair of wires.

In yet another embodiment, the end effector may further include a lead screw operatively coupled to the coupler, wherein rotation of the lead screw causes axial movement of the coupler. The end effector may further include an actuation cable, wherein the actuation cable is coupled with the lead screw for concomitant rotation therewith. The actuation cable may be slidably disposed within the central lumen of the hub.

It is contemplated that the end effector may further include a jaw support member defining a longitudinal axis, wherein the fixed jaw is securely fixed to the jaw support member. The first pivot axis may be disposed on the longitudinal axis defined by the jaw support member. The second pivot axis may be offset from the longitudinal axis defined by the jaw support member.

The moveable jaw may define a second longitudinal axis, and the first pivot axis may be spaced a first transverse distance from the second longitudinal axis and the second pivot axis may be spaced a second transverse distance from the second longitudinal axis. The second transverse distance may be greater than the first transverse distance. The first pivot axis and the second pivot axis may be parallel to one another.

The end effector may further include a lead screw operatively coupled with the coupler, wherein rotation of the lead screw, relative to the coupler, may cause axial movement of the coupler.

In accordance with still yet another embodiment of the present disclosure, an end effector for use in an endoscopic stitching device includes a fixed jaw, a moveable jaw, a coupler, a linkage member, needle engaging blades, a hub and first and second lead screws. The moveable jaw is pivotably associated with fixed jaw and is pivotable about a first pivot axis. Each jaw defines a needle receiving recess formed in a tissue contacting surface thereof and a longitudinal channel in communication with the needle receiving recess. The linkage member is pivotably associated with the moveable jaw about a second pivot axis. The needle engaging blade is slidably supported in each of the fixed jaw and the moveable jaw. Each blade is axially translatable in the longitudinal channel between a first position in which the blade partially extends across the needle receiving recess and a second position in which the blade does not extend across the needle receiving blade. The first and second lead screws are rotatably supported on the hub. The pair of needle engaging blades engages with respective first and second lead screws, wherein a rotation of the first and second lead screws causes axial translation of respective needle engaging blades, and an axial movement of the coupler causes a curvilinear movement of the linkage member causing the moveable jaw to pivot about the first pivot axis.

In an embodiment, the first and second lead screws may be configured to rotate independent of each other. The first and second lead screws may be configured to transmit independent axial translation to the pair of needle engaging blades.

BRIEF DESCRIPTION OF THE DRAWINGS

The above and other objects and features of the present disclosure will become apparent from the following description of embodiments given in conjunction with the accompanying drawings, in which.

DETAILED DESCRIPTION

Various embodiments of the presently disclosed device for endoscopic, laparoscopic, endoluminal, and/or transluminal suturing will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator.

An endoscopic suturing device generally includes a handle assembly or other suitable actuating mechanism, an elongate tubular body, a neck assembly, and an end effector. The handle assembly is connected to a proximal portion of the elongate tubular body and a neck assembly is operatively supported on a distal end of the elongate tubular body. The end effector is operatively supported at a distal end of the neck assembly, which allows the end effector to articulate in response to actuation of articulation cables. The end effector includes a suture needle and a pair of jaws. In operation, the suture needle is passed back and forth through tissue from one jaw to the other. Reference may be made to U.S. Patent Publication No. 2009/0312773, filed on Jun. 10, 2009, the entire content of which being incorporated herein by reference, for a detailed discussion of the construction and operation of an endoscopic suturing device.

Figure 1:
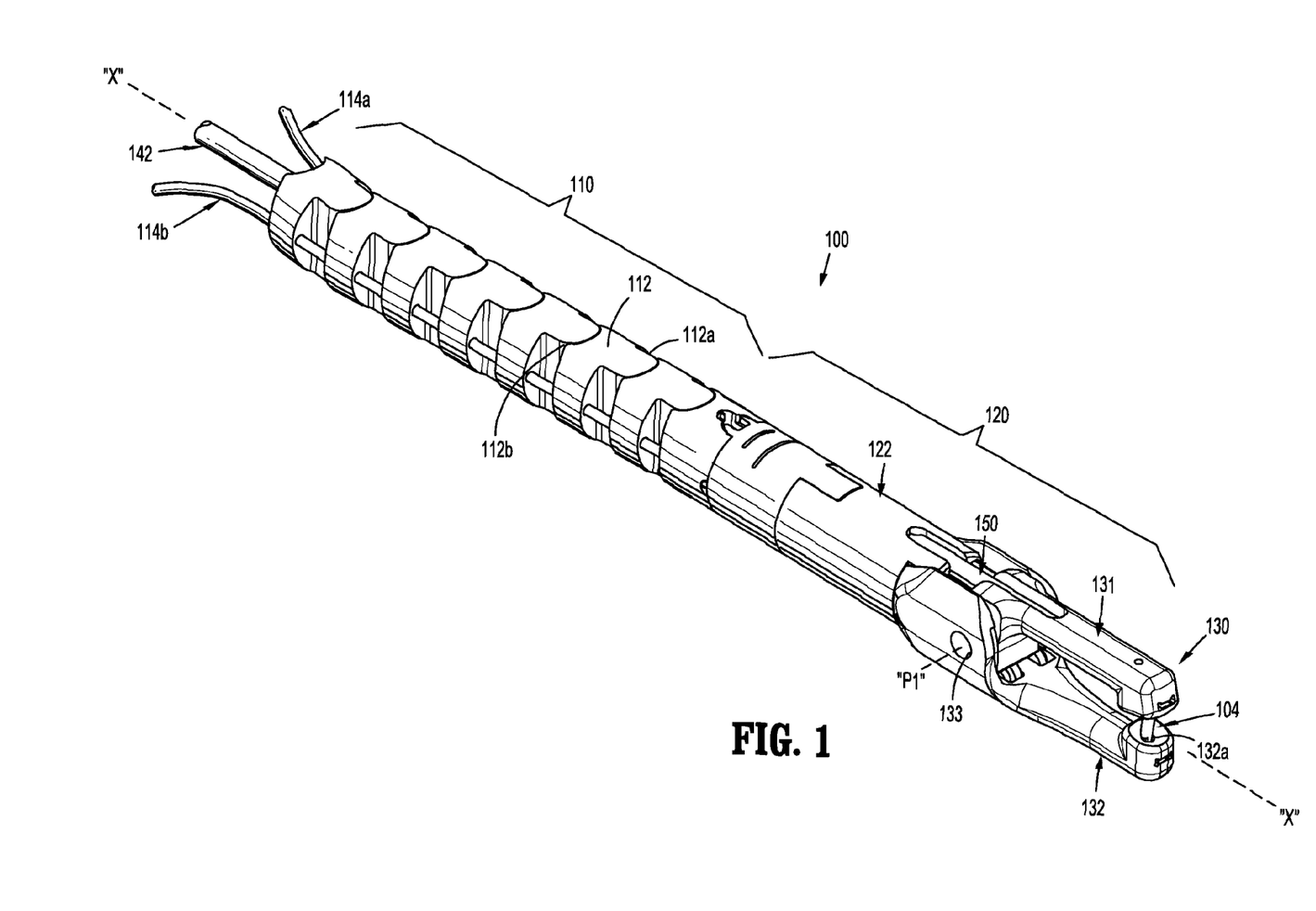
FIG. 1 is a perspective view of an end effector in accordance with an embodiment of the present disclosure for use with a surgical device.

Referring now to FIG. 1, an end effector of a stitching device in accordance with an embodiment of the present disclosure is shown generally as 100. End effector 100 is adapted to be particularly useful in endoscopic or laparoscopic procedures as end effector 100 is insertable into a surgical site, via a cannula assembly or the like. End effector 100 extends from a distal end of an elongate tubular body (not shown) extending distally from a handle assembly and defining longitudinal axis and a lumen therethrough. End effector 100 may be remotely operable by the handle assembly or other suitable actuating mechanism.

Figure 2:
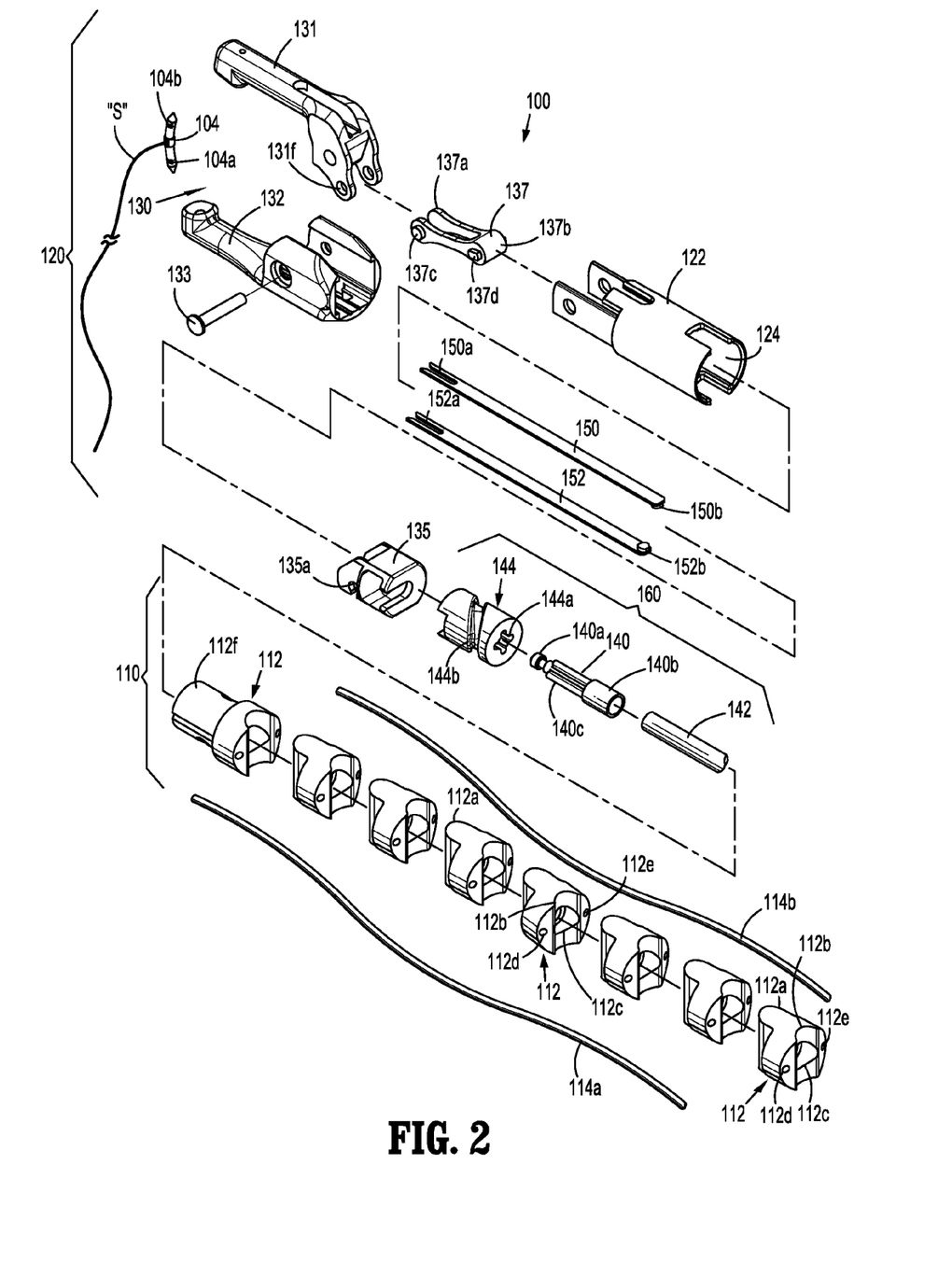
FIG. 2 is an exploded view of the end effector of FIG. 1.
Figure 3:
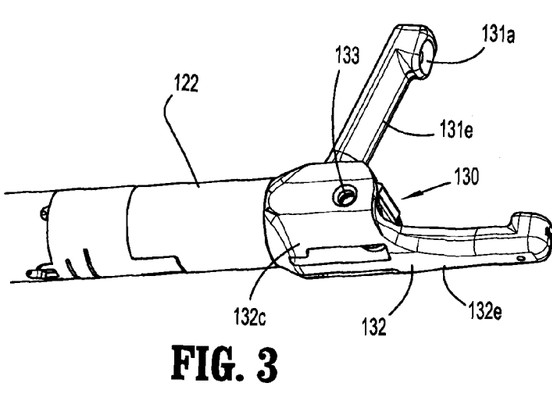
FIG. 3 is a perspective view of a tool assembly of the end effector of FIG. 1.

With reference to FIGS. 1 and 2, end effector 100 includes a neck assembly 110 and a tool assembly 120 supported on a distal end of neck assembly 110. Neck assembly 110 includes a plurality of joints 112. Each joint 112 includes a distal knuckle 112a and a proximal clevis 112b. Each knuckle 112a operatively engages a clevis 112b of an adjacent joint 112. Each joint 112 defines a central lumen 112c and a pair of opposed lumen 112d, 112e defined on either side of central lumen 112c. A pair of articulation cables 114a, 114b slidably extends through respective lumens 112d, 112e of joints 112. Distal ends of articulation cables 114a, 114b are anchored to a distal-most joint 112 at a location offset from a central axis thereof.

With reference now to FIGS. 2-5, tool assembly 120 includes a jaw assembly 130. Jaw assembly 130 includes a jaw support member 122 defining a lumen 124, a pair of jaws 131, 132, an actuation coupler 135 and a linkage member 137. Lumen 124 of jaw support member 122 is configured and dimensioned to receive a stem 112f extending from a distal-most joint 112 of neck portion 110.

Figure 4:
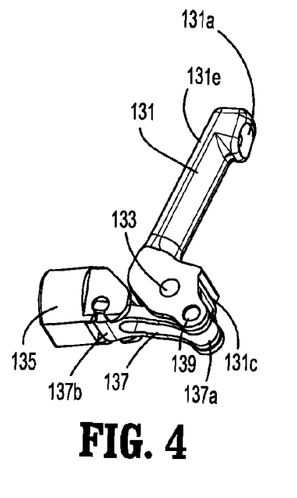
FIG. 4 is a perspective view of an actuating jaw assembly of the tool assembly of FIG. 3.
Figure 5:
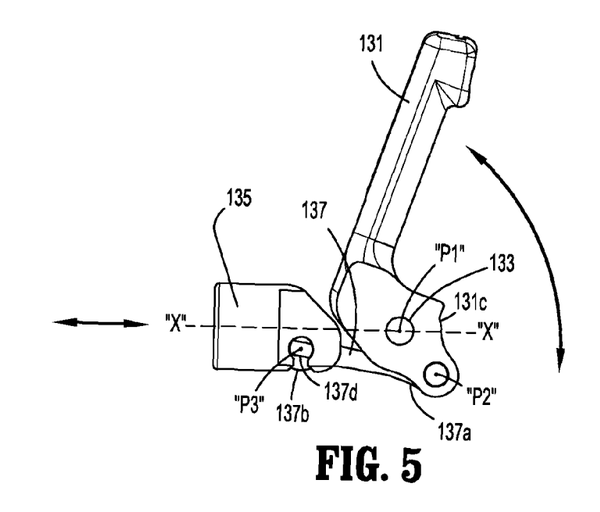
FIG. 5 is a side view of the actuating jaw assembly of FIG. 4.
Figure 6:
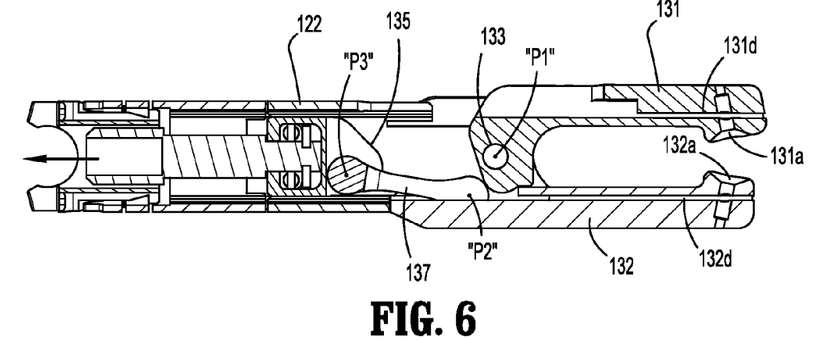
FIG. 6 is a longitudinal side cross-sectional view of the tool assembly of FIG. 3.

With reference to FIGS. 3-6, each jaw 131, 132 of jaw assembly 130 includes respective base portions 131c, 132c and respective arm portions 131e, 132e extending distally from respective base portions 131c, 132c. Each jaw 131, 132 includes a needle receiving recess 131a, 132a (as best shown in FIG. 6) configured to surround and hold at least a portion of a surgical needle 104 disposed substantially perpendicular to tissue engaging surfaces thereof. Needle 104 includes groove 104a, 104b formed near each end thereof (as shown in FIG. 2). A suture "S" may be secured to needle 104 at a location between grooves 104a, 104b. Suture "S" of needle 104 may include a one-way or barbed suture having an elongate body with a plurality of barbs extending therefrom. The barbs may be oriented in such a way that the barbs cause the suture to resist movement in a direction opposite relative to the direction in which the barb faces.

As seen in FIGS. 2, 4 and 5, base portion 131c of moveable jaw 131 extends in a direction transverse to a longitudinal axis of arm portion 131e. Base portion 131c of moveable jaw 131 defines a first pivot axis "P1" spaced a first transverse distance from the longitudinal axis of arm portion 131e, and a second pivot axis "P2" spaced a second transverse distance from the longitudinal axis of arm portion 131e. The second transverse distance to second pivot axis "P2," relative to the longitudinal axis of arm portion 131e, is greater than the first transverse distance to first pivot axis "P1." Additionally, first pivot axis "P1" and second pivot axis "P2" are parallel to one another.

With continued reference to FIGS. 2-6, base portion 132c of fixed jaw 132 is securely fixed to a distal portion of jaw support member 122, and base portion 131c of moveable jaw 131 is pivotably connected to base portion 132c of fixed jaw 132 by a pin 133 extending through first pivot axis "P1" (see FIGS. 1 and 5). First axis "P1" is disposed on a center axis "X-X" (see FIGS. 1 and 5) defined by jaw support member 122. Actuation coupler 135 is coupled to moveable jaw 131 by linkage member 137. A first end 137a of linkage member 137 is pivotably connected to base portion 131c of moveable jaw 131 at a second pivot axis "P2" which is offset a radial distance from center axis "X-X." In particular, first end 137a of linkage member 137 may include at least one protrusion member 137c pivotably received in at least one hole 131f defined in base portion 131c of moveable jaw 131 through second pivot axis "P2." A second end 137b of linkage member 137 may include a peg member 137d configured to engage a bore 135a defined at a distal end portion of actuation coupler 135. In this manner, axial movement of actuation coupler 135 (as will be discussed below) pivots moveable jaw 131 about first pivot axis "P1," relative to fixed jaw 132, thereby enabling opening and closing of the pair of jaws 131, 132. It is envisioned that the placement of second pivot axis "P2," spaced the second transverse distance from the longitudinal axis of arm portion 131e, may be tailored to provide the optimal mechanical advantage for jaw closure based on the needs of a particular procedure being performed. Furthermore, it is also contemplated that any number of bar-linkages may be used to actuate opening and closing of the pair of jaws 131, 132.

Figure 8:
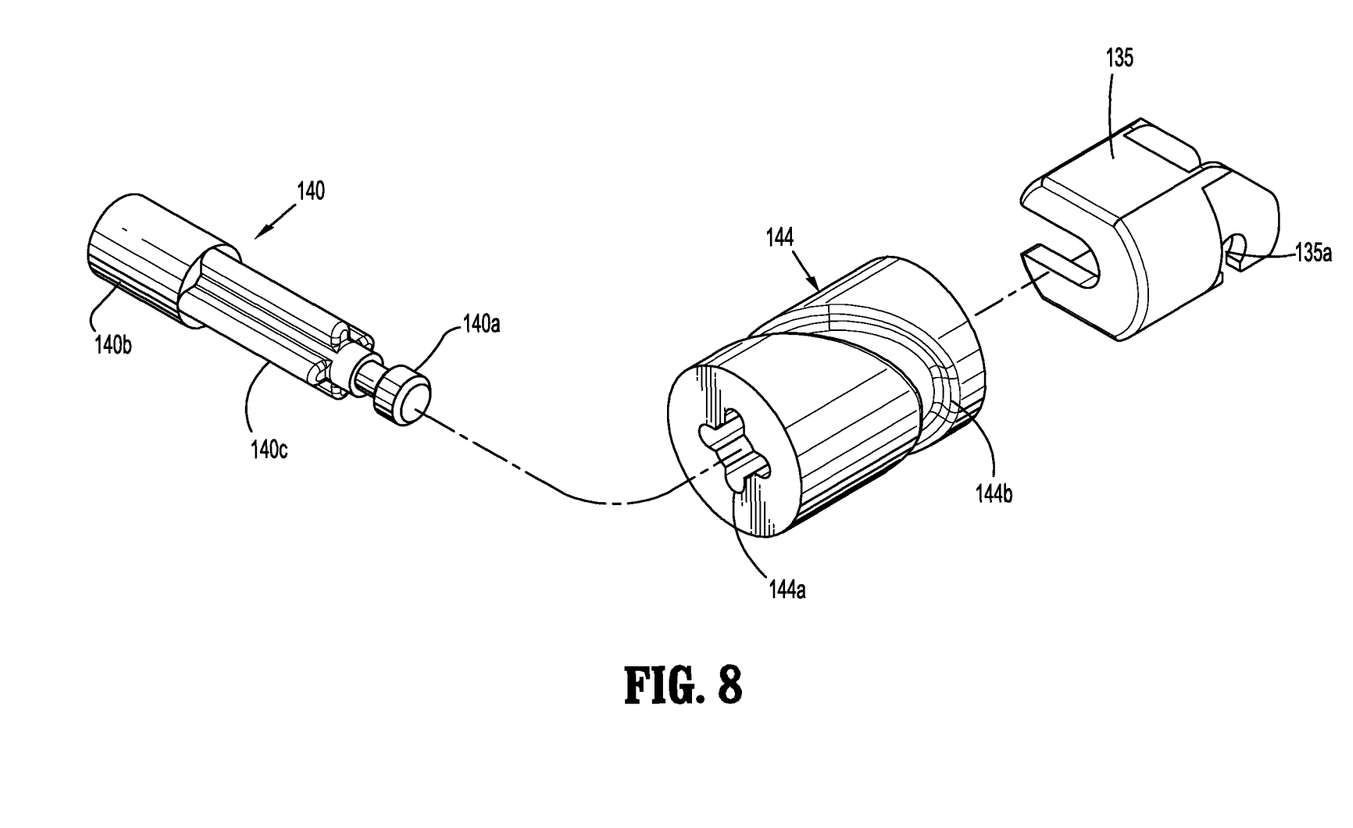
FIG. 8 is a perspective view of a blade actuation assembly for use with the end effector of FIG. 1.

With reference now to FIGS. 2 and 8, tool assembly 120 further includes a stitch actuation assembly 160. Stitch actuation assembly 160 includes a camming hub 144 configured for rotatable disposition within lumen 124 of jaw support member 122, a keyed rod 140 and an actuation cable 142. Keyed rod 140 includes a distal end 140a rotatably connected to actuation coupler 135, a proximal end 140b fixedly connected to a distal end of an actuation cable 142 and a body portion 140c having a non-circular cross-sectional profile. Camming hub 144 defines a lumen 144a therethrough configured and adapted to slidably receive body portion 140c of keyed rod 140 therein. Camming hub 144 defines a helical or spiral groove 144b in an outer surface thereof. Helical groove 144b may define various angles with respect to center axis "X-X" of jaw support member.

Camming hub 144 is configured for rotatable disposition within lumen 124 of jaw support member 122. Rotation of actuation cable 142 imparts concomitant rotation to keyed rod 140, which in turn imparts rotation to camming hub 144. However, since keyed rod 140 is rotatably connected to actuation coupler 135, no rotation is imparted to actuation coupler 135. Axial displacement of actuation cable 142 imparts axial displacement to keyed rod 140 which in turn imparts axial displacement to actuation coupler 135 of jaw assembly 130. However, since camming hub 144 is axially slidably supported on keyed rod 140, no axial displacement is imparted to camming hub 144.

Figure 9:
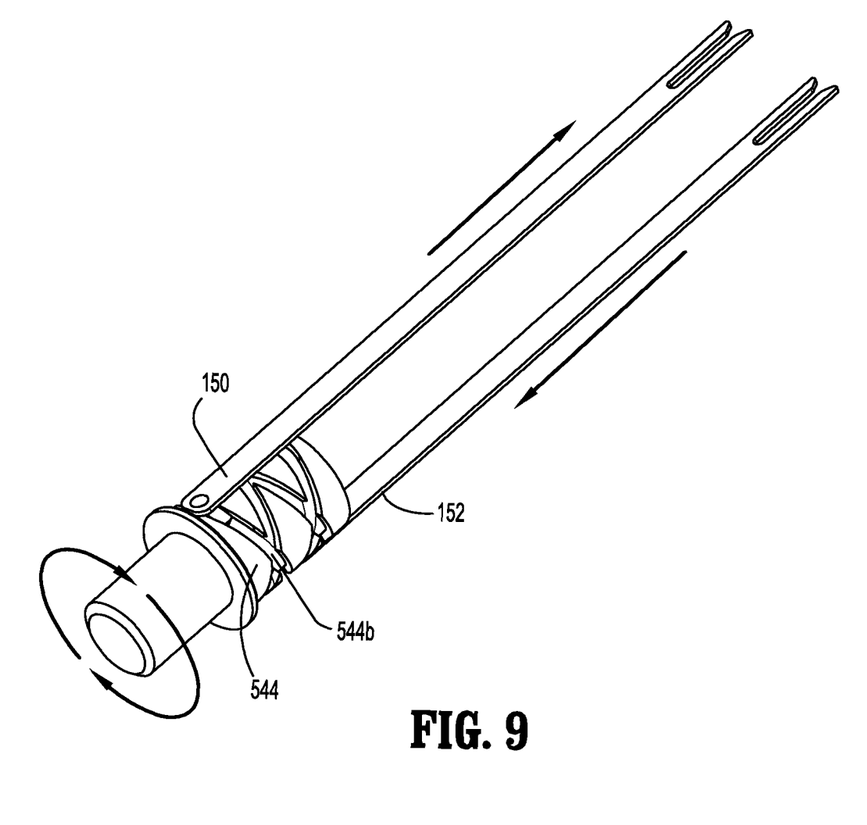
FIG. 9 is a perspective view of a blade actuation assembly in accordance with another embodiment of the present disclosure.

With particular reference now to FIGS. 2 and 6, tool assembly 120 further includes a pair of needle engaging blades 150, 152. Blades 150, 152 are slidably supported within respective channels (not shown) defined in jaw support member 122 and are extended into blade receiving channels 131d, 132d of respective jaws 131, 132. Channels 131d, 132d are dimensioned and configured to at least partially intersect needle receiving recesses 131a, 132a. Thus, by advancing blade 150 or 152 within respective channel 131d, 132d, a distal end 150a, 152a of blade 150, 152 engages or "locks in" groove 104a, 104b defined in needle 104 disposed within the respective recess 131a, 132a. Proximal ends 150b, 152b of respective blades 150, 152 are slidably disposed within groove 144b of camming hub 144. In particular, proximal ends 150b, 152b of respective blades 150, 152 may be radially opposing each other in groove 144b. In this manner, as camming hub 144 is rotated, proximal ends 150b, 152b of blades 150, 152 ride within groove 144b of camming hub 144 and are moved axially in opposite directions relative to each other. In particular, upon rotation of camming hub 144, blade 150 may move distally, while blade 152 moves proximally or vice versa. Groove 144b defined in camming hub 144 may be varied to accommodate various degrees of rotation of camming hub 144 for axial movement of respective blades 150, 152. For example, a 180-degree rotation of camming hub 144 or actuation cable 142 causes axial movement of blades 150, 152 from a proximal-most position to a distal-most position or vice versa in respective blade receiving channels 131*d*, 132*d*. However, as shown in FIG. 9, groove 544*b* defined in camming hub 544 may achieve axial movement of each blade 150, 152 from the proximal-most position to the distal-most position or vice versa, in respective blade receiving channels 131*d*, 132*d*, by a 360-degree rotation of camming hub 544.

With continued reference to FIGS. 1-6, a method of operating end effector 100 is now described. First, the pair of jaws 131, 132 is placed in an open position by having actuation coupler 135 at a distal-most position, such that actuation coupler 135 pushes linkage member 137 distally and pivots moveable jaw 131 about first pivot axis "P1" to an open position. At this time, it is assumed that needle 104 is held within needle receiving recess 131*a* by distal end 150*a* of blade 150 engaging groove 104*a* of needle 104. In order to approximate jaws 131, 132, actuation cable 142 is moved in a proximal direction, which proximally moves key rod 140 in camming hub 144. Actuation coupler 135, rotatably coupled to key rod 140, also moves proximally, thus pulling linkage member 137 proximally and causing moveable jaw 131 to pivot about first pivot axis "P1" and move the pair of jaws 131, 132 into a closed position. As the pair of jaws 131, 132 is moved to the closed position, a free end of needle 104 is moved into recess 132*a* of fixed jaw 132. If tissue were present between the pair of jaws 131, 132, the free end of needle 104 would penetrate through the tissue prior to the entrance into recess 132*a* of fixed jaw 132.

Needle 104 may then be released from moveable jaw 131 and secured or locked in fixed jaw 132, by rotating actuation cable 142, which in turn imparts rotation to keyed rod 140, which further imparts rotation to camming hub 144. As camming hub 144 is rotated proximal ends 150*b*, 152*b* of blades 150, 152 ride along or through groove 144*b*. As camming hub 144 is rotated blade 150 is moved in a proximal direction while blade 152 is moved in a distal direction. Distal end 150*a* of blade 150 disengages groove 104*a* of needle 104 disposed within recess 131*a* of moveable jaw 131, and distal end 152*b* of blade 152 engages groove 104*a* of needle 104 disposed within recess 132*a* of fixed jaw 132. Needle 104 is now secured or locked within recess 132*a* of fixed jaw 132.

Additionally, end effector 100 may be articulated about neck assembly 110, by withdrawing one of articulation cables 114*a*, 114*b* in a proximal direction. As one of the articulation cables 114*a*, 114*b* is drawn in a proximal direction, a distal end thereof, anchored to the distal-most joint 112 rotates about the interface between knuckles 112*a* and clevis 112*b* causing gaps defined therebetween, along a side surface thereof, to constrict. In order to return end effector 100 to an unarticulated condition or to articulate end effector 100 in an opposite direction the other of articulation cables 114*a*, 114*b* is withdrawn in a proximal direction.

Figure 7:
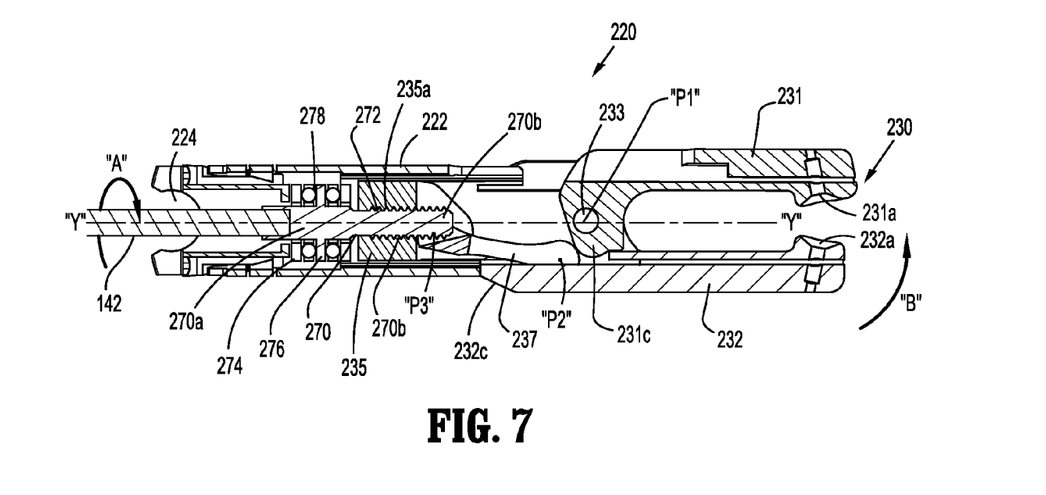
FIG. 7 is a longitudinal side cross-sectional view of a tool assembly in accordance with another embodiment of the present disclosure.

Turning now to FIG. 7, a tool assembly according to another embodiment of the present disclosure is generally designated as tool assembly 220. Tool assembly 220 is substantially similar to tool assembly 120, and thus will only be described in detail herein to the extent necessary to identify differences in construction and operation thereof. Throughout the following disclosure, like reference numerals will be used to identify like elements.

Tool assembly 220 may be supported on a distal end of neck assembly 110. Tool assembly 220 includes a jaw assembly 230 having a jaw support member 222 defining a lumen 224 therethrough, a pair of jaws 231, 232, an actuation coupler 235, a lead screw 270, and a linkage member 237.

The pair of jaws 231, 232 each include respective needle receiving recesses 231*a*, 232*a* configured to surround and hold at least a portion of surgical needle 104 disposed substantially perpendicular to tissue engaging surfaces thereof. A base portion 232*c* of fixed jaw 232 is securely fixed to a distal portion of jaw support member 222, and base portion 231*c* of moveable jaw 231 is pivotably connected to base portion 232*c* of fixed jaw 232 about a first pivot axis "P1." First pivot axis "P1" is disposed on center axis "Y-Y" defined by jaw support member 222. Actuation coupler 235 is coupled to jaw 231 by linkage member 237, such that axial movement of actuation coupler 235 pivots moveable jaw 231 about first pivot axis "P1" relative to fixed jaw 232, thereby enabling opening and closing of the pair of jaws 231, 232.

Lead screw 270 is supported in jaw support member 222 by a lead screw support 274. Lead screw support 274 defines an inner circumferential groove 278. Lead screw 270 includes an annular flange 276 projecting radially outward near a proximal portion 270*a* thereof for rotatable engagement with inner circumferential groove 278 of lead screw support 274. In this manner, the axial location of lead screw 270 is fixed with respect to support member 222. Lead screw 270 further includes threads at a distal portion 270*b* thereof for engagement with a longitudinally threaded bore 235*a* of actuation coupler 235. Proximal portion 270*a* of lead screw 270 is connected with actuation cable 142 for concomitant rotation therewith. Rotation of actuation cable 142 in the direction of arrow "A," for example, as shown in FIG. 7, causes concomitant rotation of lead screw 270 which in turn axially moves actuation coupler 235 along longitudinal axis "Y-Y." Distal axial movement of actuation coupler 235 pushes linkage member 237 distally causing moveable jaw 231 to pivot about first pivot axis "P1" in the direction of arrow "B," thereby opening the pair of jaws 231, 232. A method of operating tool assembly 220 is substantially similar to that of tool assembly 120 described above, and thus will not be discussed in further detail herein in the interest of brevity.

Figure 10:
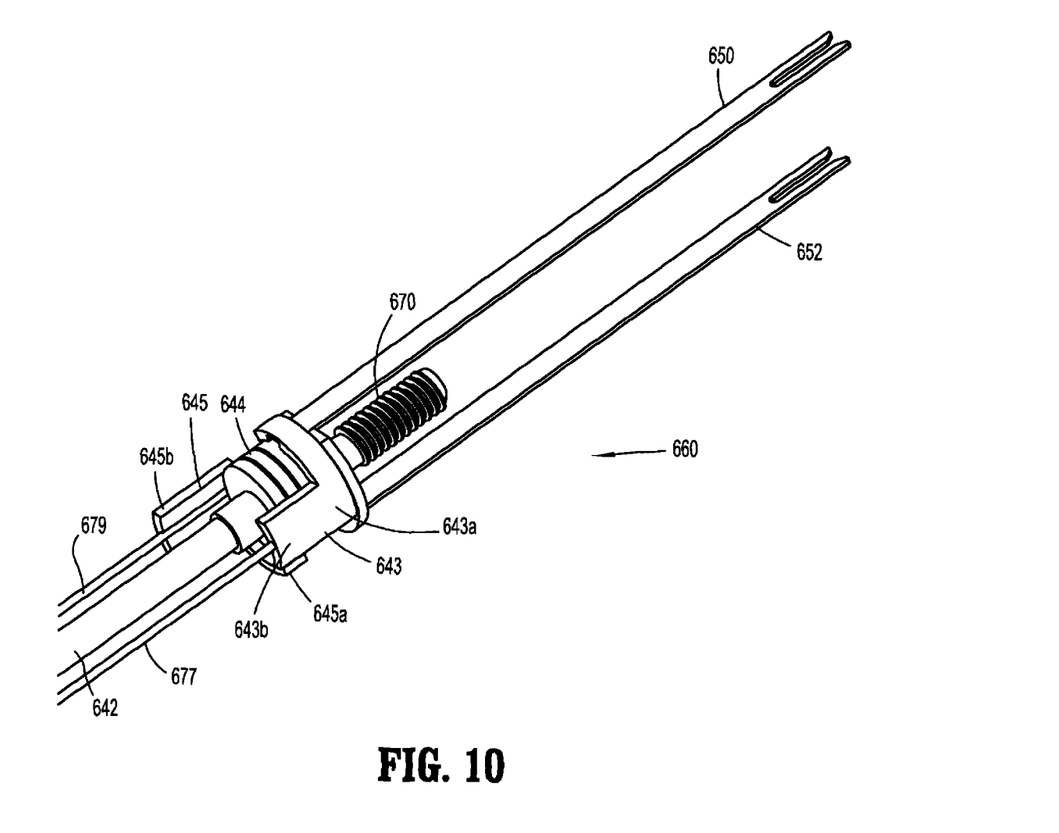
FIG. 10 is a perspective view of a blade actuation assembly in accordance with still another embodiment of the present disclosure.

In accordance with another aspect of the present disclosure, a stitch actuation assembly 660, as shown in FIG. 10, includes a pair of needle engaging blades 650, 652, a hub 644, first and second sleeves 643, 645, and first and second wires 677, 679. Hub 644 includes a bore (not shown) through which actuation cable 642 passes. Sleeves 643, 645 include opposing cuffs or partial ring portions 643*a*, 645*a*, respectively. Each opposing partial ring portion 643*a*, 645*a* at least partially circumferentially surrounds hub 644 and are each axially translatable independent with respect to each other. Sleeves 643, 645 further include guide members 643*b*, 645*b*, respectively. Guide members 643*b*, 645*b* extend proximally from respective ring portions 643*a*, 645*a* and facilitate sliding of sleeves 643, 645 on the outer surface of hub 644. The pair of needle engaging blades 650, 652 are coupled to respective ring portions 643*a*, 645*a* of first and second sleeves 643, 645. Stitch actuation assembly 660 includes first and second wires 677, 679 connected to respective guide members 643*b*, 645*b*. Wires 677, 679 may be arranged in a coaxial fashion with blades 652, 650, respectively. Actuation cable 642 may be coupled to a lead screw 670, which may operatively engage actuation coupler 235 in a manner similar to the way lead screw 270 of tool assembly 220 engages actuation coupler 235, as seen in FIG. 7.

In operation, each wire 677, 679 may be pulled or pushed to independently actuate respective blades 650, 652. However, it is also envisioned that pulling or pushing of only one of wires 677, 679 may actuate the blade of the other wire by using a combination of a rack and pinion, a pivoting yoke, etc.

Figure 11:
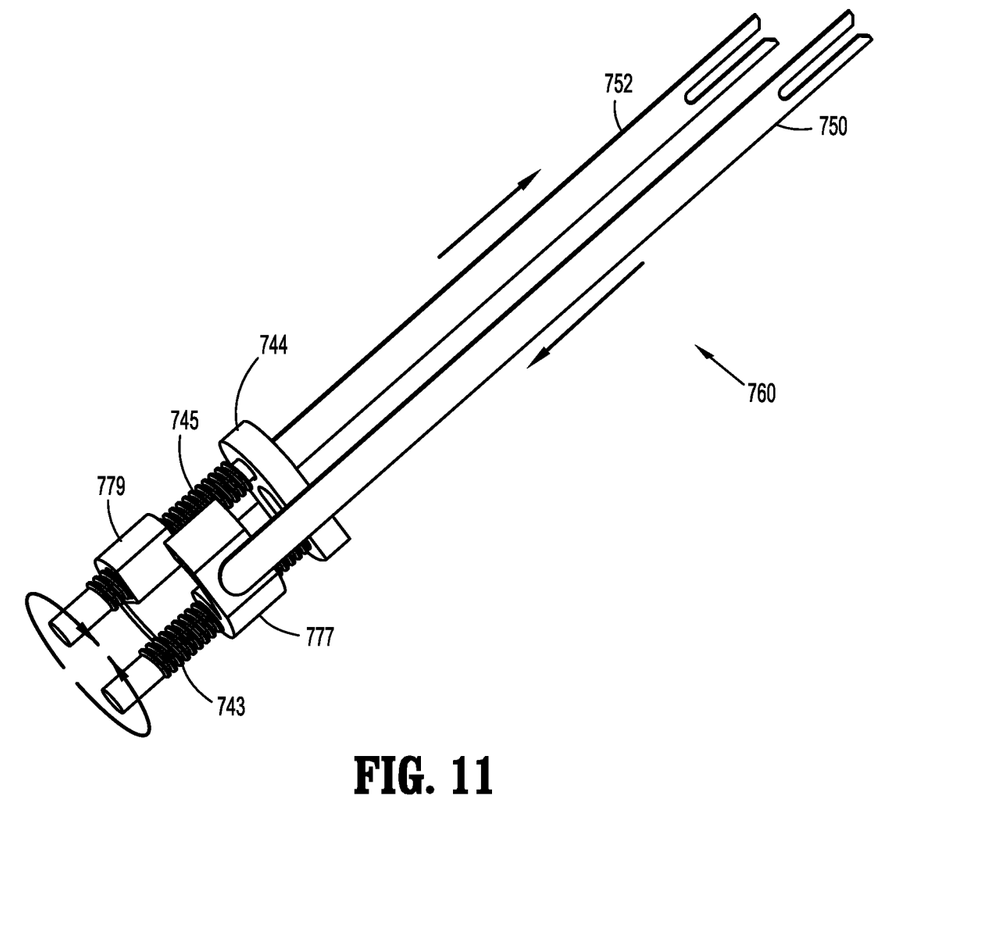
FIG. 11 is a perspective view of a blade actuation assembly in accordance with yet another embodiment of the present disclosure.

In accordance with yet another aspect of the present disclosure, a stitch actuation assembly 760, as shown in FIG. 11, includes a pair of needle engaging blades 750, 752, a support hub 744, and first and second lead screws 743, 745 rotatably connected to support hub 744. In this manner, the axial locations of first and second lead screws 743, 745 are fixed with respect to support hub 744 and rotation of each lead screw 743, 745 is not imparted to support hub 744. The pair of needle engaging blades 750, 752 includes first and second threaded members or nuts 777, 779, respectively. First and second threaded members 777, 779 are in operative engagement with first and second lead screws 743, 745, respectively.

In operation, each of first and second lead screws 743, 745 may be rotated independently to actuate respective blades 750, 752 in blade receiving channels 131*d*, 132*d* of respective jaws 131, 132. However, it is also envisioned that rotation of one of lead screws 743, 745 may also actuate the blade engaging the other lead screw by using a combination of a rack and pinion, a pivoting yoke, etc.

The surgical end effectors described above includes advantages of improved tissue approximation and more mechanical advantage during jaw closure. In addition, the lead screw jaw and blade actuation allows for a more flexible elongate tube, and thereby making the device more advantageous for endoluminal procedures.

It will be understood that various modifications may be made to the embodiments disclosed herein. Therefore, the above description should not be construed as limiting, but merely exemplifications of embodiments. Those skilled in the art will envision other modification within the scope and spirit of the claims appended thereto.

What is claimed is:

1. An end effector for use in an endoscopic stitching device, the end effector comprising:
    a fixed jaw;
    a moveable jaw pivotably associated with the fixed jaw and being pivotable about a first pivot axis, each jaw defining a needle receiving recess formed in a tissue contacting surface thereof and a longitudinal channel in communication with the needle receiving recess;
    a linkage member pivotably associated with the moveable jaw about a second pivot axis;
    a needle engaging blade slidably supported in each of the fixed jaw and the moveable jaw, each needle engaging blade being axially translatable in the longitudinal channel between a first position in which the needle engaging blade partially extends across the needle receiving recess and a second position in which the needle engaging blade does not extend across the needle receiving recess; and
    a rotatable member defining a helical groove in an outer surface thereof, a proximal end of each needle engaging blade being configured for slidable engagement in the helical groove, wherein the needle engaging blades are disposed on opposed sides of the rotatable member, wherein an axial movement of the linkage member causes the moveable jaw to pivot about the first pivot axis with respect to the fixed jaw, and rotation of the rotatable member causes opposed axial movement of the needle engaging blades.

2. The end effector according to claim 1, further comprising a lead screw operatively coupled to the linkage member, wherein rotation of the lead screw causes axial movement of the linkage member.

3. The end effector according to claim 2, further comprising a coupler operatively engaged with the lead screw, the coupler pivotally connected to the linkage member such that rotation of lead screw, relative to the coupler, axially displaces coupler and pivots the moveable jaw about the first pivot axis.

4. The end effector according to claim 1, further comprising a jaw support member defining a longitudinal axis, wherein the fixed jaw is securely fixed to the jaw support member.

5. The end effector according to claim 4, wherein the jaw support member defines a lumen configured to rotatably support the rotatable member therein and a pair of grooves configured to slidably receive respective needle engaging blades.

6. The end effector according to claim 4, wherein the first pivot axis is disposed on the longitudinal axis defined by the jaw support member.

7. The end effector according to claim 6, wherein the second pivot axis is offset from the longitudinal axis defined by the jaw support member.

8. The end effector according to claim 7, wherein the moveable jaw defines a second longitudinal axis, and wherein the first pivot axis is spaced a first transverse distance from the second longitudinal axis and the second pivot axis is spaced a second transverse distance from the second longitudinal axis, the second transverse distance being greater than the first transverse distance.

9. The end effector according to claim 7, wherein the first pivot axis and the second pivot axis are parallel to one another.

10. The end effector according to claim 4, further comprising a lead screw operatively coupled with linkage member, wherein rotation of the lead screw, relative to the linkage member, causes axial movement of the linkage member.

11. The end effector according to claim 10, wherein the lead screw includes an annular flange projecting radially outward for rotatable engagement with the jaw support member.

12. The end effector according to claim 11, wherein the jaw support member defines an inner circumferential groove for receiving the annular flange of the lead screw therein.

13. The end effector according to claim 1, further comprising an actuation cable coupled to the linkage member, the actuation cable being slidably movable through a longitudinal bore defined in the rotatable member.

14. The end effector according to claim 1, wherein unidirectional rotation of the rotatable member results in axial translation of the needle engaging blades in opposite directions to each other.

\* \* \* \* \*